United States Patent
Handfield

(10) Patent No.: US 9,199,694 B2
(45) Date of Patent: Dec. 1, 2015

(54) SLIDE BAR FOR A TRACK SYSTEM

(75) Inventor: Robert Handfield, St-Lucien (CA)

(73) Assignee: Kimpex Inc., Drummondville, Quebec (CA)

( * ) Notice: Subject to any disclaimer, the term of this patent is extended or adjusted under 35 U.S.C. 154(b) by 468 days.

(21) Appl. No.: 13/170,977

(22) Filed: Jun. 28, 2011

(65) Prior Publication Data

US 2012/0160150 A1     Jun. 28, 2012

Related U.S. Application Data

(60) Provisional application No. 61/359,531, filed on Jun. 29, 2010.

(51) Int. Cl.
| | |
|---|---|
| *G01D 21/00* | (2006.01) |
| *B62M 27/02* | (2006.01) |
| *G01N 3/56* | (2006.01) |
| *F16D 66/02* | (2006.01) |
| *E21B 12/02* | (2006.01) |

(52) U.S. Cl.
CPC ......... *B62M 27/02* (2013.01); *B62M 2027/026* (2013.01); *E21B 12/02* (2013.01); *F16D 66/02* (2013.01); *G01D 21/00* (2013.01); *G01N 3/56* (2013.01)

(58) Field of Classification Search
CPC .. B62M 27/02; B62M 2027/026; G01N 3/56; F16D 66/02; E21B 12/02; G01D 21/00
USPC .................... 116/208; 138/36, 104, 110, 137; 305/43, 46, 185
See application file for complete search history.

(56) References Cited

U.S. PATENT DOCUMENTS

| | | | | |
|---|---|---|---|---|
| 3,138,224 | A | * | 6/1964 | White .............................. 188/78 |
| 3,578,055 | A | * | 5/1971 | French et al. .............. 152/154.2 |
| 3,623,900 | A | * | 11/1971 | Nelson et al. ................. 427/386 |
| 3,729,041 | A | * | 4/1973 | Kubota ......................... 152/523 |
| 4,119,123 | A | * | 10/1978 | Samuels ....................... 138/122 |
| 4,226,274 | A | * | 10/1980 | Awaya et al. .............. 152/154.2 |
| 4,474,217 | A | * | 10/1984 | DeMarse et al. ............. 138/137 |
| 5,228,478 | A | * | 7/1993 | Kleisle .......................... 138/104 |
| 5,511,636 | A | * | 4/1996 | Tanaka .................... 188/1.11 W |
| 5,628,393 | A | * | 5/1997 | Steeber et al. ............. 198/699.1 |
| 6,220,199 | B1 | * | 4/2001 | Williams ...................... 116/208 |
| 6,354,668 | B2 | * | 3/2002 | Okajima et al. ......... 301/95.102 |
| 6,418,873 | B1 | * | 7/2002 | Chen ............................. 116/208 |

(Continued)

OTHER PUBLICATIONS

Dewent Abstract for DE 102007003504, Krueger et al. "Brake lining for disk brake of motor vehicle wheel, has wear indicators for local optical wear indication, where wear indicator includes color storage for freely setting dyestuffs, if wear indicators is exposed to rubbing wear", published Jul. 31, 2008.*

(Continued)

*Primary Examiner* — R. A. Smith
*Assistant Examiner* — Tania Courson
(74) *Attorney, Agent, or Firm* — Robert Brouillette; Brouillette & Partners

(57) ABSTRACT

A slide bar for the track system of a snowmobile or an all-terrain vehicle comprises colored, or otherwise visually distinctive, wear indicating marks extending longitudinally along at least one of the side walls thereof. The colored wear indicating marks generally provide an indication to the operator of the vehicle that the slide bar needs to be replaced.

20 Claims, 3 Drawing Sheets

(56) References Cited

U.S. PATENT DOCUMENTS

| | | | |
|---|---|---|---|
| 6,494,543 B1* | 12/2002 | Hashimura et al. | 301/95.101 |
| 6,494,548 B2* | 12/2002 | Courtemanche | 305/168 |
| 6,523,586 B1* | 2/2003 | Eromaki et al. | 152/154.2 |
| 6,609,770 B2* | 8/2003 | Gauthier | 305/167 |
| 6,709,138 B1* | 3/2004 | Johnson | 362/500 |
| 6,769,746 B2* | 8/2004 | Rodgers et al. | 305/166 |
| 6,955,189 B1* | 10/2005 | Weyker | 138/104 |
| 7,011,126 B2* | 3/2006 | Heinen | 152/154.2 |
| 7,424,936 B2* | 9/2008 | McClellan | 188/1.11 W |
| 7,731,306 B2* | 6/2010 | Busley et al. | 305/46 |
| 7,918,514 B2* | 4/2011 | Dal Pra' | 301/95.103 |
| 8,011,739 B2* | 9/2011 | Busley | 305/46 |
| 8,424,435 B2* | 4/2013 | Sudmalis et al. | 83/485 |
| 8,955,925 B2* | 2/2015 | Bessette et al. | 305/142 |
| 2002/0050741 A1* | 5/2002 | Gauthier | 305/165 |
| 2003/0034690 A1* | 2/2003 | Hori et al. | 305/191 |
| 2003/0094854 A1* | 5/2003 | Rodgers et al. | 305/166 |
| 2003/0138655 A1* | 7/2003 | Watanabe et al. | 428/523 |
| 2004/0065377 A1* | 4/2004 | Whiteley | 138/104 |
| 2007/0119363 A1* | 5/2007 | Neto et al. | 116/208 |
| 2007/0295432 A1* | 12/2007 | Posada et al. | 152/154.2 |

OTHER PUBLICATIONS

Derwent Abstract, DE 26909119 U1, Expresso Deut Transportgeraete "Slide Rail for sack barrow to slide over steps using u-section with embedded coloured indicator for wear of sliding surface.", publshed Sep. 25, 1997.*

* cited by examiner

SLIDE BAR FOR A TRACK SYSTEM

CROSS-REFERENCE TO RELATED APPLICATIONS

The present patent application claims the benefits of priority of U.S. Provisional Patent Application No. 61/359,531, entitled "Slide Bar for a Track System" and filed at the United States Patent and Trademark Office on Jun. 29, 2010, the content of which is incorporated herein by reference.

FIELD OF THE INVENTION

The present invention generally relates to the field of snowmobiles, all-terrain vehicles ("ATV" or "ATVs"), and utility terrain vehicle ("UTV" or "UTVs"), and more particularly to the field of track systems for snowmobiles, ATVs and UTVs.

BACKGROUND OF THE INVENTION

Snowmobiles are propelled using an endless track mounted about a track suspension system. To reduce friction between the travelling track and the suspension system, the latter is typically provided with one or more slide bars made from low friction materials such as polymeric materials (e.g. UHMW polyethylene).

However, slide bars are subjected to substantial wear and tear and need to be replaced regularly.

Still, it is difficult of the snowmobile operators to know exactly when the slide bars need to be replaced.

Some slide bars are provided with grooves or ridges extending along the length of the side walls thereof and providing an indication of the wear thereof. However, due to the harsh environments in which snowmobiles are used and operated, these grooves or ridges often fade and become difficult to discern with the passage of time. Also, these grooves or ridges, being the same color, are difficult to discern from a standing position on the side of the snowmobile. These grooves or ridges thus fail to provide a clear and trustworthy indication of the need the replace the slide bars. Hence, slide bars with wear indicating grooves or ridges are not satisfactory.

Slide bars are also used in track systems used to replace wheels on generally wheeled vehicles such as ATVs and UTVs. Still, these slide bars suffer the same problems as the slide bars used on snowmobiles.

Hence, there is a need for a slide bar with improved wear indicating marks.

SUMMARY OF THE INVENTION

According to one aspect of the present invention, a slide bar for a track system having the slide bar extending longitudinally and being made from polymeric material is disclosed. The slide bar comprising a first longitudinally extending side wall, a second longitudinally extending side wall, and a longitudinally extending underside, at least one of the first and second side walls comprising at least one wear indicating mark visually distinctive from a surface of the at least one of the first and second side walls, the at least one wear indicating mark extending longitudinally along the at least one of the first and second side walls, wherein said slide bar connects a traveling track to a suspension rail system of a snowmobile.

According to another aspect of the present invention, a slide bar for a track system having the slide bar extending longitudinally and being made from polymeric material having a first color is disclosed. The slide bar comprising a first longitudinally extending side wall, a second longitudinally extending side wall, and a longitudinally extending underside, the first side wall comprising at least one first longitudinally extending groove, the second side wall comprising at least one second longitudinally extending groove, the at least one first groove having mounted therein a first longitudinally extending insert having a second color different from the first color being as such visually distinctive from a surface of the first longitudinally extending side wall, and the at least one second groove having mounted therein a second longitudinally extending insert having a third color different from the first color and being as such visually distinctive from a surface of the second longitudinally extending side wall, wherein said slide bar connects a traveling track to a suspension rail system of a snowmobile.

BRIEF DESCRIPTION OF THE DRAWINGS

The above and other objects, features and advantages of the invention will become more readily apparent from the following description, reference being made to the accompanying drawings in which.

DETAILED DESCRIPTION OF THE PREFERRED EMBODIMENT

A novel slide bar 130 for a track system will be described hereinafter. Although the invention is described in terms of specific illustrative embodiments, it is to be understood that the embodiments described herein are by way of example only and that the scope of the invention is not intended to be limited thereby.

Figure 1:
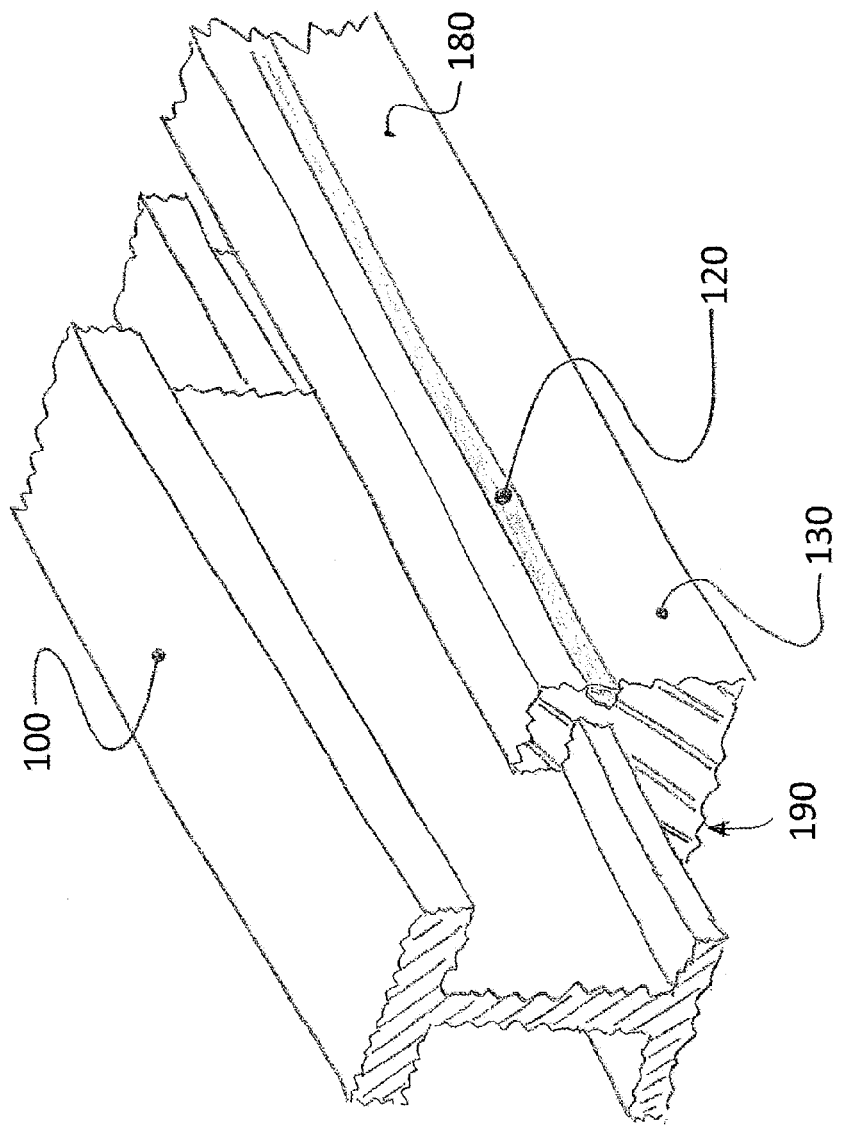
FIG. 1 is a fragmentary perspective view of an exemplary slide bar mounted to a suspension rail in accordance with the principles of the present invention.
Figure 2:
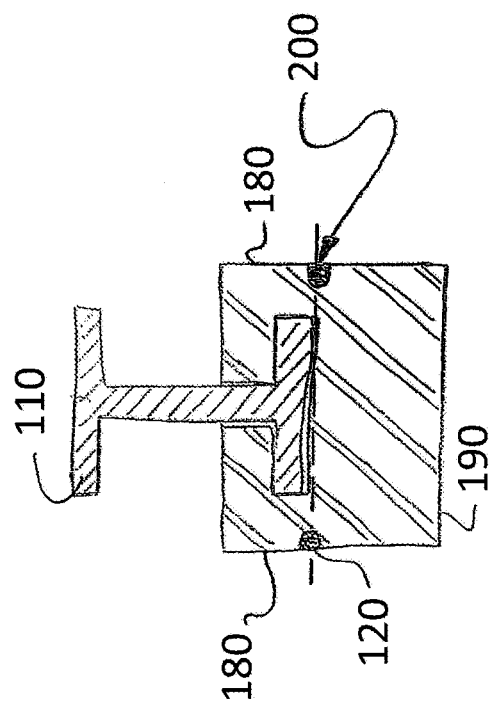
FIG. 2 is a cross-sectional view of the slide bar and suspension rail of FIG. 1.
Figure 3:
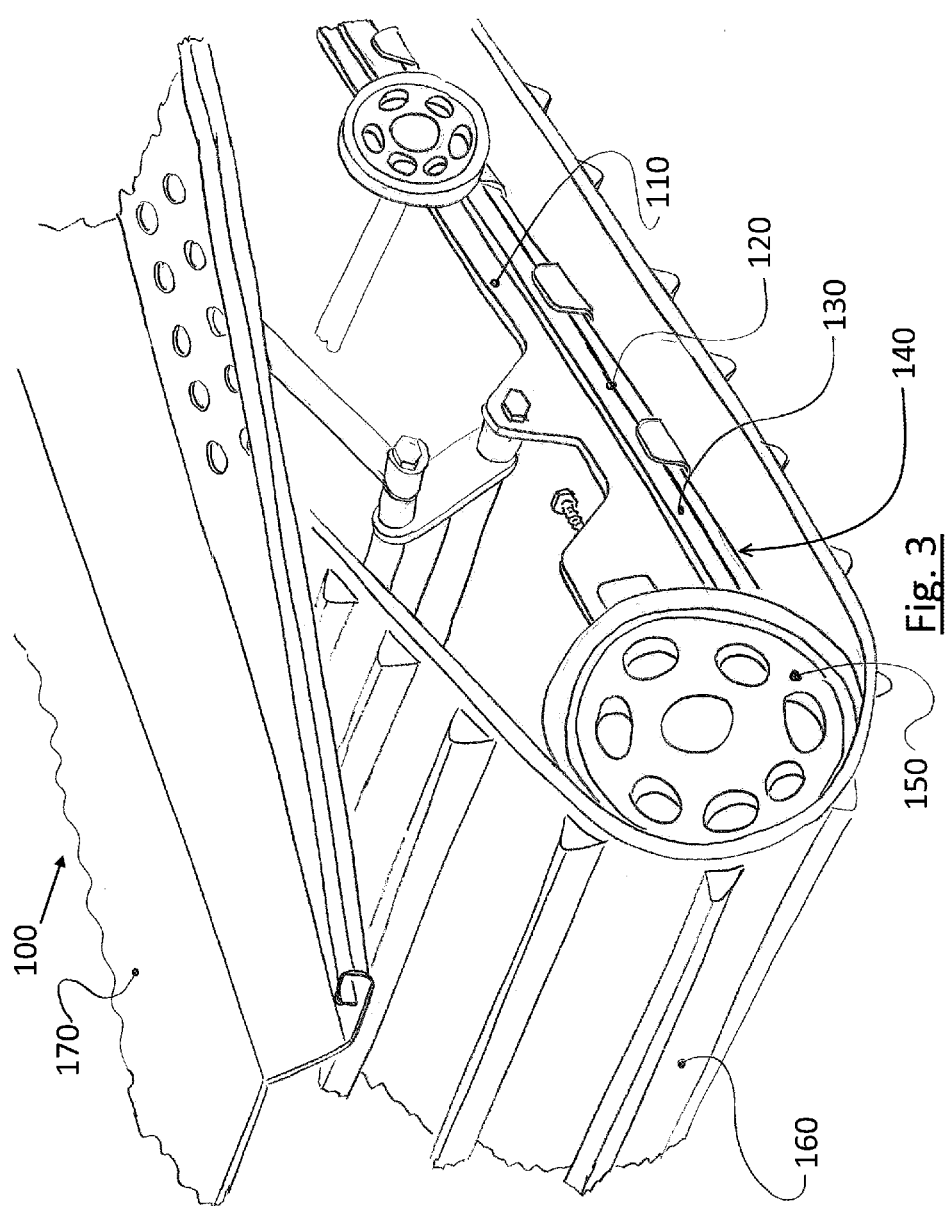
FIG. 3 is a fragmentary perspective view of an exemplary slide bar mounted to a suspension rail on a snowmobile track in accordance with the principles of the present invention.

Referring to FIGS. 1 to 3, a portion of a typical suspension rail 110 of a snowmobile 100 rear suspension system is shown. Conventionally, a slide bar 130, or wear bar, is mounted to the suspension rail 100 to decrease friction between the suspension rail 100 and the traction band or the clips mounted thereto. Similar slide bars 130 are sometimes mounted to the frames of track systems used to replace wheels on normally wheeled vehicles such as ATVs and UTVs. Hence, even though the present embodiment is described in the context of a suspension rail 110 for a snowmobile 100, the present invention is not limited to slide bars 130 for used on snowmobile 100 track 160 systems.

Under normal conditions, the slide bar 130 wears due to the repeated sliding contacts between the traction band and the underside 190 of the slide bar 130. Hence, it is generally necessary to replace the slide bar 130 since it is a wear item.

In accordance with the principles of the present invention, at least one and preferably both side walls of the slide bar 130 are provided with wear indicating marks 120 or wear markers 120. Furthermore, these wear indicating marks 120 are visually distinct from the rest of the slide bar 130 such as to provide a visually clear indication of the necessity to replace the slide bar 130.

In the present embodiment, the wear indicating marks 120 are of a color distinct from the color of the material of the slide bar 130 such that even if the side walls of the slide bar 130 are worn or damaged, the wear indicating marks 120 will remain visible.

As best illustrated in FIG. 1, the wear indicating marks 120 extend longitudinally along the length of the slide bar 130. Moreover, as shown in FIG. 2, the wear indicating marks 120 are generally positioned on the side walls at substantially the same level or height as the bottom surface of the suspension rail 110. Hence, when the slide bar 130 has worn up to the wear indicating marks 120, it is generally necessary to replace the slide bar 130 to avoid damaging the suspension rail 100 and/or the traction band.

Though the wear indicating marks 120 are shown as being continuous lines, in alternate embodiments, the wear indicating marks 120 could possibly be discontinuous lines (e.g. dashed lines, dotted lines, etc.).

In the present embodiment illustrated in FIGS. 1 and 2, the wear indicating marks 120 are colored polymeric inserts secured into grooves formed, etched and/or otherwise machined into the side walls of the slide bar 130. Understandably, as mentioned above, the inserts are of a color significantly different from the color of the slide bar 130 material such as to provide an easier visual inspection.

In the present embodiment, now referring to FIG. 2, a cross-sectional view of the suspension rail 110 within the slide bar 130 is shown. In this embodiment, the marker is in line with the bottom of the rail 200. In this exemplary embodiment, the wear marker 120 is present on both side wall of the slide bar 130.

In the present embodiment, now referring to FIG. 3, the slide bar 130 is shown on a snowmobile 100 track. In this exemplary embodiment, the snowmobile 100 has an aluminum tunnel 170 covering the rubber track 160. The track system comprises a rear idler wheel 150 operatively connected to the traveling track 140 having the slide bar 130 located thereto. The slide bar 130 has the rear suspension rail 110 slideably mounted therein. As such, as the slide bar 130 wear due to the sliding of the rear suspension rail 110, the user may use the colored wear marker 120 to assess the wear of the slide bar 130.

In alternate embodiments, the wear indicating marks 120 could be directly fastened on the side walls of the slide bar 130 with suitable fasteners (e.g. screws, glue, etc.). Understandably, the present invention is not limited to any particular manner of mounting the wear indicating marks 120 to the side walls of the slide bar 130.

In still alternate embodiments, one or both side walls could be provided with multiple parallel wear indicating marks 120 each positioned at a different level or height. These multiple wear indicating marks 120 would preferably all be of different colors (e.g. lower green-colored marks indicating low wear, middle yellow-colored marks indicating intermediate wear and higher red-colored marks indicating critical wear and the need for replacement) and/or of different line types (e.g. lower white dotted marks, middle or intermediate white dashed marks, and higher continuous marks) such as to provide an indication of the degree of wear of the slide bar 130.

While illustrative and presently preferred embodiments of the invention have been described in detail hereinabove, it is to be understood that the inventive concepts may be otherwise variously embodied and employed and that the appended claims are intended to be construed to include such variations except insofar as limited by the prior art.

The invention claimed is:

1. A slide bar for a track system, the slide bar extending longitudinally and being made from polymeric material, the slide bar comprising a first longitudinally extending side wall, a second longitudinally extending side wall, and a longitudinally extending underside, at least one of the first and second side walls comprising at least one wear indicating mark visually distinctive from a surface of the at least one of the first and second side walls, the at least one wear indicating mark extending longitudinally along the at least one of the first and second side walls, wherein said slide bar connects a traveling track to a suspension rail system of a snowmobile.

2. A slide bar as claimed in claim 1, wherein the slide bar has a first color, wherein the at least one wear indicating mark has a second color, and wherein the first and second colors are different.

3. A slide bar as claimed in claim 1, wherein the at least one of the first and second side walls is the first side wall, wherein the at least one wear indicating mark is at least one first wear indicating mark, and wherein the second side wall comprises at least one second wear indicating mark visually distinctive from the second side wall, the at least one second wear indicating mark extending longitudinally along the second side wall.

4. A slide bar as claimed in claim 3, wherein the at least one first wear indicating mark and the at least one second wear indicating mark are located at the same level on the slide bar.

5. A slide bar as claimed in claim 3, wherein the first side wall comprises a first longitudinally extending groove, wherein the second side wall comprises a second longitudinally extending groove, wherein the at least one first wear indicating mark is a first insert located in the first groove, and wherein the at least one second wear indicating mark is a second insert located in the second groove.

6. A slide bar as claimed in claim 5, wherein the first insert and the second insert are made from polymeric material.

7. A slide bar as claimed in claim 6, wherein the slide bar has a first color, wherein the first insert has a second color, wherein the second insert has a third color, and wherein the second and third colors are different from the first color.

8. A slide bar as claimed in claim 5, wherein the first and second grooves are located at the same level on the slide bar.

9. A slide bar as claimed in claim 1, wherein the at least one of the first and second side walls comprising the at least one wear indicating mark comprises a longitudinally extending groove, and wherein the at least one wear indicating mark is an insert located in the groove.

10. A slide bar as claimed in claim 9, wherein the insert is made from polymeric material.

11. A slide bar as claimed in claim 10, wherein the slide bar has a first color, wherein the insert has a second color, and wherein the first and second colors are different.

12. A slide bar as claimed in claim 1, wherein the at least one of the first and second side walls comprises at least two wear indicating marks visually distinctive from the at least one of the first and second side walls, the at least two wear indicating marks being parallel and extending longitudinally along the at least one of the first and second side walls.

13. A slide bar as claimed in claim 12, wherein the at least two wear indicating marks are visually distinctive from each other.

14. A slide bar as claimed in claim 12, wherein the at least two wear indicating marks have different colors.

15. A slide bar as claimed in claim 1, wherein the slide bar is configured to be mounted to a rail of the track system, and wherein the at least one wear indicating mark is substantially aligned with a bottom of the rail when the slide bar is mounted to the rail.

16. A slide bar for a track system, the slide bar extending longitudinally and being made from polymeric material having a first color, the slide bar comprising a first longitudinally extending side wall, a second longitudinally extending side wall, and a longitudinally extending underside, the first side wall comprising at least one first longitudinally extending groove, the second side wall comprising at least one second longitudinally extending groove, the at least one first groove having mounted therein a first longitudinally extending insert having a second color different from the first color being as such visually distinctive from a surface of the first longitudinally extending side wall, and the at least one second groove having mounted therein a second longitudinally extending insert having a third color different from the first color and being as such visually distinctive from a surface of the second longitudinally extending side wall, wherein said slide bar connects a traveling track to a suspension rail system of a snowmobile.

17. A slide bar as claimed in claim 16, wherein the first longitudinally extending insert is made from polymeric material, and wherein the second longitudinally extending insert is made from polymeric material.

18. A slide bar as claimed in claim 16, wherein the at least one first groove and the at least one second groove are located at the same level on the slide bar.

19. A slide bar as claimed in claim 16, wherein the slide bar is configured to be mounted to a rail of the track system, and wherein the at least one first groove is substantially aligned with a bottom of the rail when the slide bar is mounted to the rail.

20. A slide bar as claimed in claim 16, wherein the slide bar is configured to be mounted to a rail of the track system, and wherein both the at least one first groove and the at least one second groove are substantially aligned with a bottom of the rail when the slide bar is mounted to the rail.

* * * * *